(12) United States Patent
Aoki

(10) Patent No.: US 8,495,905 B2
(45) Date of Patent: Jul. 30, 2013

(54) GAS CONCENTRATION DETECTION DEVICE

(75) Inventor: Keiichiro Aoki, Numazu (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 805 days.

(21) Appl. No.: 12/721,641

(22) Filed: Mar. 11, 2010

(65) Prior Publication Data

US 2010/0229628 A1  Sep. 16, 2010

(30) Foreign Application Priority Data

Mar. 11, 2009  (JP) ................... 2009-058614

(51) Int. Cl.
*G01N 27/41* (2006.01)
*G01N 27/416* (2006.01)

(52) U.S. Cl.
USPC .......... 73/23.31; 204/425; 204/426; 204/427; 204/431

(58) Field of Classification Search
USPC ............ 73/23.31, 23.32; 204/424–429, 431
See application file for complete search history.

(56) References Cited

U.S. PATENT DOCUMENTS 7,182,846 B2 * 2/2007 Mizutani et al. .............. 204/427

FOREIGN PATENT DOCUMENTS

| JP | 2001124730 A | 5/2001 |
|---|---|---|
| JP | 2003149201 A | 5/2003 |
| JP | 2004053579 A | 2/2004 |
| JP | 2005241540 A | 9/2005 |
| JP | 2007155605 A | 6/2007 |

* cited by examiner

*Primary Examiner* — Daniel Larkin
(74) *Attorney, Agent, or Firm* — Gifford, Krass, Sprinkle, Anderson & Citkowski, P.C.

(57) ABSTRACT

A gas concentration detection device includes: a first sensor having a resistance layer exposed to a gas, and an electrode covered by the resistance layer, the first sensor producing an output according to a gas component ratio on the electrode surface; and a second sensor having a pump cell that pumps oxygen into a gas chamber that contains part of the gas or discharges oxygen out of the gas chamber, and a sensor cell that produces an output according to a gas component ratio in the gas within the gas chamber, the second sensor producing an output based on the pump cell current when the pump cell is operated such that the output of the sensor cell is a predetermined value; and a hydrogen concentration detection unit that detects a hydrogen concentration in the gas based on an output difference between the first sensor output and the second sensor output.

7 Claims, 3 Drawing Sheets

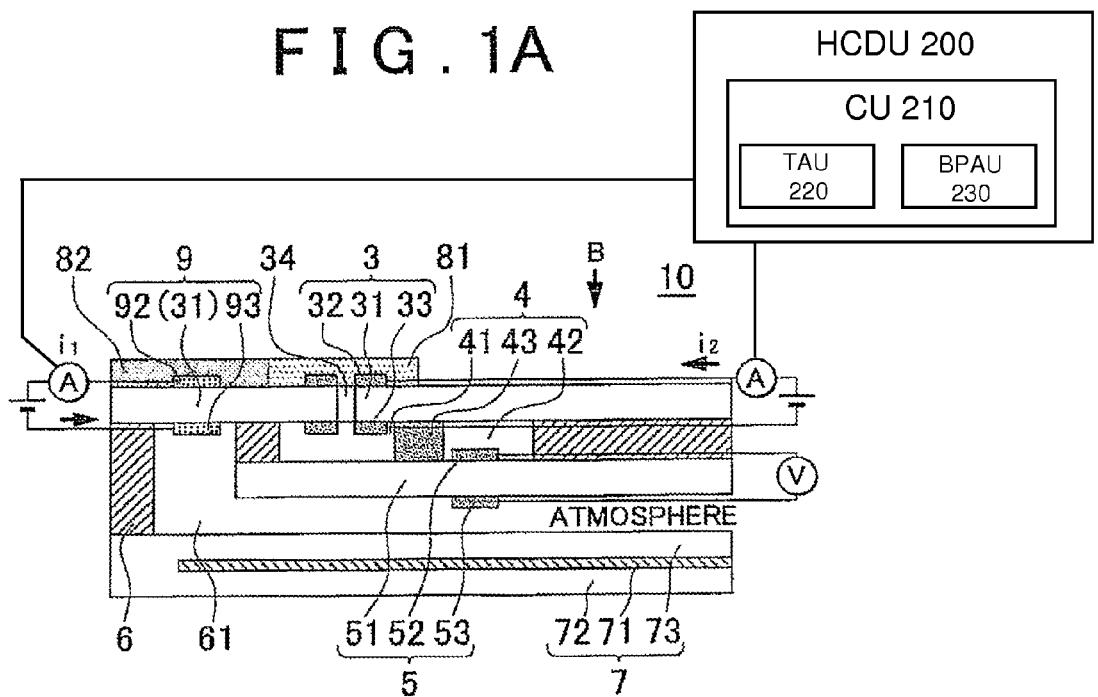
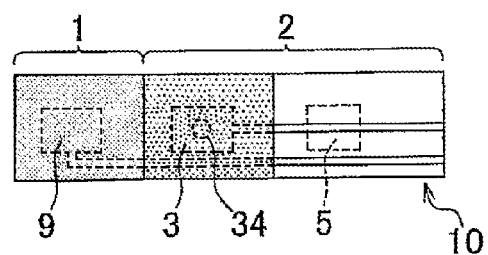

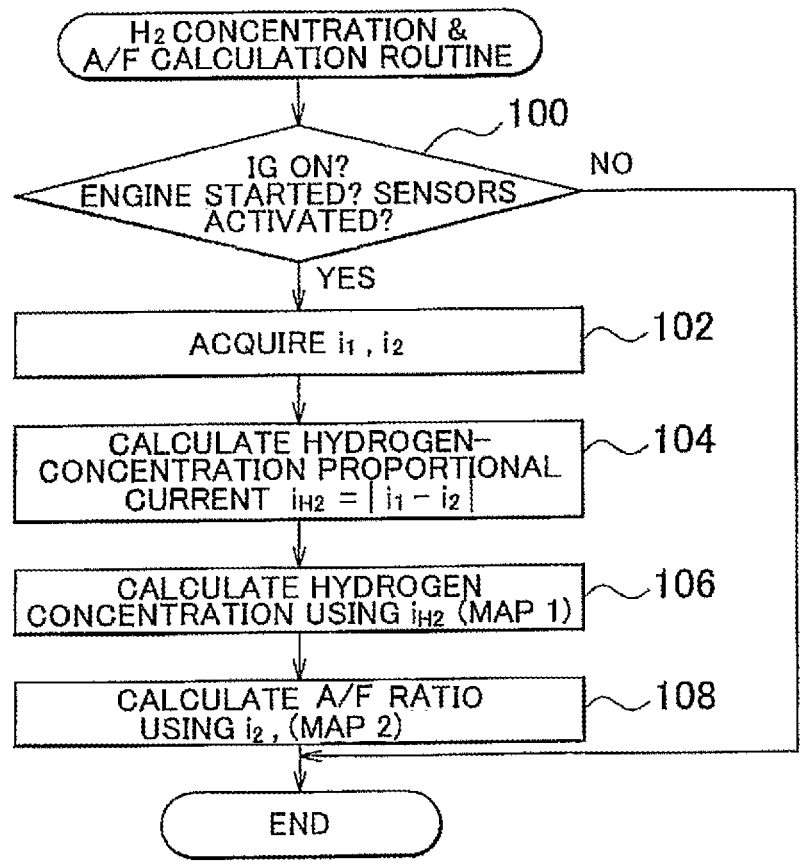

GAS CONCENTRATION DETECTION DEVICE

INCORPORATION BY REFERENCE

The disclosure of Japanese Patent Application No. 2009-058614 filed on Mar. 11, 2009 including the specification, drawings and abstract is incorporated herein by reference in its entirety.

BACKGROUND OF THE INVENTION

1. Field of the Invention

The invention relates to a gas concentration detection device, and more particularly to a gas concentration detection device that detects the concentration of a specific component in exhaust gas discharged by an internal combustion engine.

2. Description of the Related Art

For instance, Japanese Patent Application Publication No. 2007-155605 (JP-A-2007-155605) describes an exhaust gas sensor system that detects the concentration of a specific component in exhaust gas of an internal combustion engine. This system has two sets of sensor cells. Each sensor cell has a diffusion resistance layer exposed to exhaust gas, and an electrode covered by the diffusion resistance layer. The sensor cells function as limiting-current type air-fuel (A/F) ratio sensors that produce an output in accordance with a gas component ratio on the electrode surface. On the surface of the diffusion resistance layer of one of the sensor cells (first cell), in particular, there is provided a catalyst layer for promoting decomposition and reaction of a hydrogen ($H_2$) component.

In such a system, the $H_2$ component contained in the exhaust gas is eliminated as the $H_2$ reacts in the catalyst layer of one sensor cell (first cell). In the first cell, as a result, a sensor output from which the influence of the $H_2$ component has been eliminated is detected. The other sensor cell (second cell), by contrast, has no catalyst layer, and hence the $H_2$ component may penetrate into the diffusion resistance layer. The $H_2$ component, having a high diffusion rate, reaches the electrode surface in a greater amount than that of oxidizing agents such as oxygen ($O_2$) or nitrogen oxide (NOx). As a result, a sensor output denoting a richer A/F ratio than the actual A/F ratio is detected in the second cell, on account of the influence of the $H_2$ component. $H_2$ concentration is detected in the above conventional system on the basis of the difference between these sensor outputs.

In the above conventional system, however, the oxidation reaction of the $H_2$ component in the catalyst layer may be restricted under conditions of a rich exhaust gas, i.e. under conditions in which the oxidizing agents in the exhaust gas are insufficient. The above conventional system, therefore, is limited to instances where the exhaust gas environment is lean and $H_2$ concentration can be detected with good precision, and thus cannot readily cope with a wider variety of exhaust gas environments.

SUMMARY OF THE INVENTION

The invention provides a gas concentration detection device that allows detecting $H_2$ concentration in an exhaust gas with good precision, in various exhaust gas environments.

In a first aspect of the invention, a gas concentration detection device includes: a first sensor having a resistance layer exposed to a gas to be detected, and an electrode covered by the resistance layer, the first sensor producing an output according to a gas component ratio on the surface of the electrode; a second sensor having a pump cell that pumps oxygen into a gas chamber that contains part of the gas to be detected or discharges oxygen out of the gas chamber, and a sensor cell that produces an output according to a gas component ratio in the gas to be detected within the gas chamber, the second sensor producing an output on the basis of a current flows through the pump cell when the pump cell is operated such that the output of the sensor cell is a predetermined value; and a hydrogen concentration detection unit that detects a hydrogen concentration in the gas to be detected on the basis of an output difference between the output of the first sensor and the output of the second sensor.

The hydrogen component contained in the gas to be detected has a characteristically higher diffusion rate than that of other components, in particular oxidizing agents such as $O_2$ or NOx. Therefore, a greater amount of $H_2$ than of $O_2$ reaches the surface of the electrode covered by the diffusion layer of the first sensor, even if $H_2$ and $O_2$ reach the surface of the diffusion layer in a balanced proportion. As a result, the output of the first sensor indicates an A/F ratio in the exhaust gas that is richer than the actual A/F ratio, on account of the influence of the $H_2$ component. In the second sensor, by contrast, oxygen is pumped in or discharged out by the pump cell, to adjust thereby a predetermined oxygen excess in the gas to be detected that is taken up into the gas chamber. As a result, a high $H_2$ component equilibration capability is maintained even when a rich gas, low in $O_2$ component, is taken up into the gas chamber. The output of the second sensor, therefore, is unaffected by the $H_2$ component, and indicates at all times values that correspond to the actual A/F ratio in the gas to be detected.

In the first aspect of the invention, thus; the influence of the $H_2$ component in the gas to be detected is reflected only on the output of the first sensor. Accordingly, the output difference between the output of the first sensor and the output of the second sensor is correlated to the concentration of $H_2$ component in the gas to be detected. In the first aspect, therefore, the hydrogen concentration in the gas to be detected can be detected with good precision on the basis of the output difference between the two sensors. Hydrogen concentration can be detected as a result in various exhaust gas environments, with good precision and unaffected by the A/F ratio of the gas to be detected.

In the first aspect, the hydrogen concentration detection unit may include a correction unit that corrects a relationship between the output difference and the hydrogen concentration on the basis of a state quantity of the gas to be detected.

The output difference between the output of the first sensor and the output of the second sensor changes with changing conditions, such as the temperature, back pressure or the like of the gas to be detected, even if the hydrogen concentration in the gas to be detected remains unchanged. By way of the above configuration, the relationship between hydrogen concentration and output difference is corrected on the basis of the state quantity of the gas to be detected. Hydrogen concentration can be detected as a result with good precision regardless of the state of the gas to be detected.

In the above configuration, the correction unit may include a temperature acquisition unit that acquires the temperature of the gas to be detected, and performs correction such that as the acquired temperature rises, the hydrogen concentration corresponding to the output difference increases.

In the above configuration, the relationship between the output difference and hydrogen concentration is corrected such that as the temperature of the gas to be detected rises, the hydrogen concentration corresponding to the output difference increases. Hydrogen concentration can be detected as a result with good precision regardless of the temperature of the gas to be detected.

In the above configuration, the correction unit may include a back pressure acquisition unit that acquires a back pressure of the gas to be detected, and performs correction such that as the acquired back pressure increases, the hydrogen concentration corresponding to the output difference increases.

In the above configuration, the relationship between the output difference and hydrogen concentration is corrected such that as the back pressure of the gas to be detected increases, the hydrogen concentration corresponding to the output difference increases. Hydrogen concentration can be detected as a result with good precision regardless of the back pressure of the gas to be detected.

In the first aspect, the second sensor may further include a diffusion layer that separates the gas chamber into a first gas chamber in which an electrode of the sensor cell is exposed, and a second gas chamber in which an electrode of the pump cell is exposed, wherein the resistance layer and the diffusion layer may have gas diffusion characteristics such that the state quantity of the gas that reaches the surface of the electrode of the sensor cell is equivalent to the state quantity of the gas that reaches the surface of the electrode of the first sensor.

In the above configuration, the diffusion characteristics of the resistance layer and of the diffusion layer are adjusted such that the state quantity of the gas to be detected that reaches the electrode surface of the first sensor is equivalent to the state quantity of the gas to be detected that reaches the electrode surface of the second sensor. As a result, the dependence on the state quantity of the gas to be detected is equalized between the first sensor and the second sensor, and hence hydrogen concentration can be detected without correcting individually each sensor.

In the first aspect, the first sensor and the second sensor may be formed integrally with each other.

In such a configuration, the first sensor and the second sensor are formed integrally with each other, which allows reducing part counts and lowering manufacturing costs.

BRIEF DESCRIPTION OF THE DRAWINGS

The foregoing and further objects, features and advantages of the invention will become apparent from the following description of example embodiments with reference to the accompanying drawings, wherein like numerals are used to represent like elements and wherein:

FIGS. 1A and 1B are diagrams for explaining the configuration of a gas concentration detection device 10 according to an embodiment of the invention;

FIG. 2 is a flowchart of a routine executed in the embodiment of the invention;

FIG. 3 is a map indicating the relationship between a sensor current difference $i_{H2}$ and $H_2$ concentration;

FIG. 4 is a map indicating the relationship between a sensor current $i_2$ and an A/F ratio.

DETAILED DESCRIPTION OF THE EMBODIMENTS

Figure 5A:
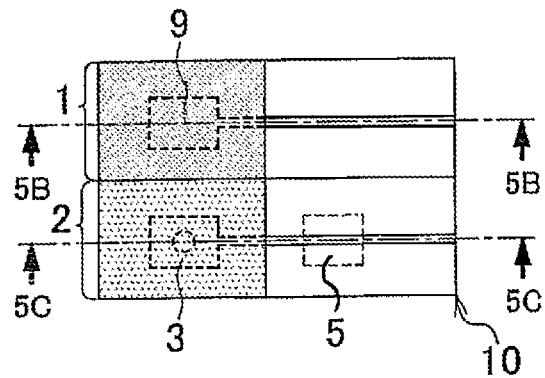
FIGS. 5A to 5C are diagrams illustrating a modification of the structure of the gas concentration detection device 10.

An explanation follows first on the configuration of the gas concentration detection device according to an embodiment of the invention, with reference to FIGS. 1A and 1B. FIGS. 1A and 1B are diagrams for explaining the configuration of a gas concentration detection device 10 according to the embodiment. More specifically, FIG. 1A is a cross-sectional diagram of the gas concentration detection device 10, and FIG. 1B is a diagram of the gas concentration detection device 10 viewed in the direction of arrow B in FIG. 1A. The gas concentration detection device 10 illustrated in FIGS. 1A and 1B is a hydrogen concentration detection unit 200 that detects the concentration of the $H_2$ component in exhaust gas discharged from an internal combustion engine. The hydrogen concentration detection unit 200 includes a correction unit 210 that includes a temperature acquisition unit 220 and a back pressure acquisition unit 230.

As illustrated in FIG. 1B, the gas concentration detection device 10 has a first sensor 1 and a second sensor 2. Both the first sensor 1 and the second sensor 2 function as A/F ratio sensors that detect a current corresponding to the A/F ratio of the exhaust gas. The features of the two sensors are explained in detail below.

The configuration of the second sensor 2 will be explained in detail first, with reference to FIGS. 1A and 1B. The second sensor 2 is formed through sequential stacking of a pump cell 3, a spacer 4, a sensor cell 5, a spacer 6 and a heater 7. The pump cell 3 has the function of pumping $O_2$ in and out. The pump cell 3 has a solid electrolyte body 31, and a first pump electrode 32 and second pump electrode 33 disposed so as to sandwich the solid electrolyte body 31. The solid electrolyte body 31, which is an element, has $O_2$ ion conductivity, and uses a sheet of zirconium oxide ($ZrO_2$), hafnium oxide ($HfO_2$), thorium dioxide ($ThO_2$), bismuth oxide ($BiO_3$) or the like. The first pump electrode 32 and second pump electrode 33 disposed so as to sandwich the solid electrolyte body 31 can be formed, for instance, by screen printing.

The first pump electrode 32 formed on the surface of the solid electrolyte body 31 is exposed to a space where exhaust gas, as the gas to be detected, is present, namely an exhaust passage of the engine. For instance, a porous cermet electrode which includes a noble metal such as platinum (Pt) may be used as the first pump electrode 32.

Meanwhile, the second pump electrode 33 which is formed on the back surface of the solid electrolyte body 31, namely on the opposite side of the solid electrolyte body 31 from the first pump electrode 32, is exposed to a below-described first inner space 41. For instance, a porous cermet electrode which includes a noble metal such as Pt may be used as the second pump electrode 33.

A pinhole 34, as an inlet hole, is formed in the pump cell 3, running through the solid electrolyte body 31, the first pump electrode 32 and the second pump electrode 33. The hole diameter of the pinhole 34 is designed in such a manner that the diffusion rate of the exhaust gas introduced into the below-described first inner space 41 via the pinhole 34 is a predetermined diffusion rate. The first inner space 41 communicates with a space where the gas to be detected is present, via the pinhole 34 and a below-described porous protective layer 81.

The porous protective layer 81 is formed on the surface of the solid electrolyte body 31. The porous protective layer 81 covers the surface of the first pump electrode 32, including the pinhole 34, as well as the surroundings of the first pump electrode 32. The porous protective layer 81 may be formed, for instance, of porous alumina. The porous protective layer 81 allows suppressing poisoning of the first pump electrode 32 and allows suppressing clogging of the pinhole 34 on account of soot or the like contained in, the exhaust gas.

In the spacer 4 there is formed the above-described first inner space 41 and a second inner space 42. The two inner spaces 41, 42 communicate with each other via a diffusion resistance layer 43. The diffusion resistance layer 43 can be formed, for instance, of porous alumina.

The sensor cell 5 has a solid electrolyte body 51, and a first sensor electrode 52 and a second sensor electrode 53 disposed so as to sandwich the solid electrolyte body 51. The first sensor electrode 52 and the second sensor electrode 53 are formed, for instance, by screen printing.

The first sensor electrode 52 formed on the surface of the solid electrolyte body 51 is exposed to the second inner space 42. For instance, a porous cermet electrode which includes a noble metal such as Pt may be used as the first sensor electrode 52.

Meanwhile, the second sensor electrode 53 formed on the back surface of the solid electrolyte body 51, namely on the opposite side of the solid electrolyte body 51 from the first sensor electrode 52 is exposed to an atmosphere duct 61 fanned in the spacer 6. Atmospheric air gets into the atmosphere duct 61. For instance, a porous cermet electrode which includes a noble metal such as Pt may be used as the second sensor electrode 53. The atmosphere duct 61 may be formed by providing a cutout in the spacer 6.

The heater 7 has insulating layers 72, 73 formed into sheets and a heater electrode 71 buried between the insulating layers 72, 73. The insulating layers 72, 73 are formed, for instance, of a ceramic such as alumina. The heater electrode 71 is formed, for instance, of a cermet of Pt and a ceramic such as alumina.

The configuration of the first sensor 1 will be explained next in detail. The first sensor 1 is formed integrally with the second sensor 2, through sequential stacking of a sensor cell 9, the spacer 6 and the heater 7. The sensor cell 9 has the above-described solid electrolyte body 31, and a first sensor electrode 92 and a second sensor electrode 93 disposed so as to sandwich the solid electrolyte body 31. The first sensor electrode 92 and the second sensor electrode 93 are formed, for instance, by screen printing.

The first sensor electrode 92 formed on the surface of the solid electrolyte body 31 is exposed to a space where exhaust gas, as the gas to be detected, is present, namely an exhaust passage of the engine. For instance, a porous cermet electrode which includes a noble metal such as Pt may be used as the first sensor electrode 92.

Meanwhile, the second sensor electrode 93 formed on the back surface of the solid electrolyte body 31, namely on the opposite side of the solid electrolyte body 31 from the first sensor electrode 92 is exposed to the above-mentioned atmosphere duct 61. For instance, a porous cermet electrode which includes a noble metal such as Pt may be used as the second sensor electrode 93.

A diffusion resistance layer 82 having a porous material is formed on the surface of the solid electrolyte body 31. The diffusion resistance layer 82 covers the surface of the first sensor electrode 92 and the surroundings thereof. The diffusion resistance layer 82 may be formed, for instance, of porous alumina. The diffusion resistance layer 82 allows suppressing poisoning of the first sensor electrode 92. The porosity, pore size distribution, specific surface area relative to the electrode and so forth of the diffusion resistance layer 82 are determined on the basis of a relationship with the diffusion resistance layer 43. More specifically, the thickness, the volume and so forth of the diffusion resistance layers are adjusted in such a manner that the state of the exhaust gas (temperature, back pressure and the like, detected by the temperature acquisition unit 220 and the back pressure acquisition unit 230, respectively, of the correction unit 210) that reaches the surface of the first sensor electrode 92 is equivalent to that of the exhaust gas that reaches the first sensor electrode 52, in other words, in such a manner that the diffusion distance and specific surface area of the diffusion resistance layers with respect to the respective electrodes are the same ratios.

The operation mechanism of the first sensor 1 will be explained first. The first sensor 1 functions as a so-called one-cell limiting-current type A/F ratio sensor. The diffusion resistance layer 82 is exposed to exhaust gas inside the exhaust passage. The various components in the exhaust gas reach the surface of the diffusion resistance layer 82 and diffuse then into the latter.

The exhaust gas contains reducing agents such as carbon monoxide (CO), $H_2$, hydrocarbon (HC) and the like, and oxidizing agents such as $O_2$, NOx and the like. These components react completely with each other through combustion during the process of reaching the surfaces of the first sensor electrode 92 and the second sensor electrode 93, and through combustion after having reached the surfaces. Both oxidizing and reducing agents are eliminated if a stoichiometric A/F ratio is realized. By contrast, residual reducing agents survive in the case of a rich A/F ratio, and oxidizing agents in the case of a lean A/F ratio.

When voltage is applied from the second sensor electrode 93 to the first sensor electrode 92 in the sensor cell 9, $O_2$ remaining in the first sensor electrode 92 is pumped to the second sensor electrode 93. On the other hand, when reducing agents remain in the first sensor electrode 92, $O_2$ That is required for eliminating these reducing agents is pumped from the second sensor electrode 93 towards the first sensor electrode 92. As a result, a first sensor current $i_1$, corresponding to the ratio between reducing agents and oxidizing agents that reach the surface of the first sensor electrode 92, i.e. corresponding to the A/F ratio in the surface of the first sensor electrode 92, is generated in the sensor cell 9. The first sensor 1 detects the A/F ratio of the exhaust gas on the basis of the first sensor current $i_1$.

The operation mechanism of the second sensor 2 is explained next. The second sensor 2 functions as a so-called two-cell limiting-current type A/F ratio sensor. The porous protective layer 81 is exposed to the exhaust gas inside the exhaust passage. As described above, the exhaust gas contains reducing agents and oxidizing agents. The various components in the exhaust gas reach the surface of the porous protective layer 81, diffuse then into the latter, and are led to the first inner space 41 via the pinhole 34. The amount of exhaust gas that gets into the first inner space 41 is determined on the basis of the diffusion resistance of the porous protective layer 81 and the pinhole 34.

The exhaust gas, into or out of which $O_2$ has been pumped by the pump cell 3, diffuses into the diffusion resistance layer 43, and is led to the second inner space 42. An electromotive force Vs corresponding to the ratio between the partial pressure of $O_2$ in the second inner space 42 and the partial pressure of $O_2$ in the atmosphere duct 61 is generated in the sensor cell 5. The second sensor 2 is configured so that a second sensor current $i_2$ flows through the pump cell 3 in such a manner that the electromotive force Vs is a predetermined reference voltage Vc, i.e. in such a manner that the A/F ratio in the first inner space 41 and the second inner space 42 is maintained constant. More specifically, adjustment is carried out in such a manner that the second sensor current $i_2$ is zero when the A/F ratio of the exhaust gas introduced into the first inner space 41 is the stoichiometric A/F ratio, and in such a manner that a second sensor current $i_2$ ($i_2>0$) flows so that $O_2$ is discharged out of the first inner space 41 when the A/F ratio is lean, and, by contrast, a second sensor current $i_2$ ($i_2<0$) flows so that $O_2$ is pumped into the first inner space 41 when the A/F ratio of the exhaust gas is rich. The second sensor 2 detects the A/F ratio of the exhaust gas on the basis of the second sensor current $i_2$.

The $H_2$ concentration detection principle used by the hydrogen concentration detection unit 200 in the gas concentration detection device 10 of the embodiment will be explained next. The $H_2$ component contained in the exhaust gas has a characteristically higher diffusion rate than that of other components, in particular oxidizing agents such as $O_2$ or NOx. Therefore, assuming for instance that $H_2$ and $O_2$ reach the surface of the diffusion resistance layer 82 in a balanced proportion, then a greater amount of $H_2$ than of $O_2$ reaches the surface of the first sensor electrode 92.

When $H_2$, which is a reducing agent, reaches the surface of the first sensor electrode 92 in a greater amount than that of $O_2$, which is an oxidizing agent, the reducing agent becomes overabundant in the vicinity of the surface, and the A/F ratio becomes enriched in the surroundings. In this case, therefore, the first sensor current $i_1$ generated in the sensor cell 9 is influenced by the $H_2$ component and takes on, as a result, a current that indicates that the A/F ratio is rich, even if the A/F ratio of the exhaust gas is the stoichiometric A/F ratio.

In the second sensor 2, by contrast, $O_2$ is replenished by the pumping action of the pump cell 3 until the $O_2$ component in the first inner space 41 is at a predetermined ratio (stoichiometric A/F ratio), even when an enriched gas, low in $O_2$ component, gets into the first inner space 41. That is, the $O_2$ ratio in the inner space 41 is kept constant at all times, regardless of the A/F ratio of the exhaust gas that is introduced. As a result, this allows maintaining at all times a high capability of equilibrating the $H_2$ component in the inner space 41.

In such a second sensor 2, the $H_2$ component in the exhaust gas that is introduced into the first inner space 41 disappears in the process of getting into the second inner space 42 by diffusing across the diffusion resistance layer 43. As a result, the exhaust gas reaches the surface of the first sensor electrode 52 after an equilibration reaction between the $H_2$ component and the $O_2$ component. The output of the sensor cell 5 is thus a value from which the influence of the $H_2$ component in the exhaust gas has been eliminated. As described above, the second sensor current $i_2$ that flows through the pump cell 3 is set on the basis of the output of the sensor cell 5. The second sensor current $i_2$, therefore, is not influenced by the $H_2$ component in the exhaust gas, and is accordingly a current that indicates an accurate A/F ratio.

The influence of the $H_2$ component contained in the exhaust gas is reflected thus only in the first sensor current $i_1$ of the first sensor 1. The influence is greater the higher the $H_2$ concentration in the exhaust gas is. Herein, the difference between the first sensor current $i_1$ of the first sensor 1 and the second sensor current $i_2$ of the second sensor 2 is correlated to the concentration of the $H_2$ component in the exhaust gas by the hydrogen concentration detection unit 200. Therefore, the hydrogen concentration detection unit 200 can detect the $H_2$ concentration with good precision in the gas concentration detection device 10 of the embodiment on the basis of the sensor current difference $i_{H2}=|i_1-i_2|$ calculated by the hydrogen concentration detection unit 200. Specifically, the hydrogen concentration detection unit 200 detects the $H_2$ concentration in the gas to be detected on the basis of an output difference between the received first sensor current $i_1$ and the second sensor current $i_2$.

The relationship between the sensor current difference $i_{H2}$ and $H_2$ concentration changes depending on the state quantity of the exhaust gas (such as one of temperature and back pressure acquired by the temperature acquisition unit 220 and the back pressure acquisition unit 230, respectively). Therefore, the detection precision of $H_2$ concentration by the hydrogen concentration detection unit 200 can be further enhanced by the correction unit which corrects the sensor current difference $i_{H2}$ on the basis of the state quantity of the exhaust gas. More specifically, the sensor current difference $i_{H2}$ is corrected by the correction unit 210 to be greater for a higher temperature of the exhaust gas, acquired by the temperature acquisition unit 220, that reaches the surface of the first sensor electrode 52 and the surface of the first sensor electrode 92. As the correction unit 210 corrects the sensor current difference $i_{H2}$ to be greater the higher the temperature of the exhaust gas, acquired by the temperature acquisition unit 220, the hydrogen concentration $H_2$ is increased as the temperature increases. The sensor current difference $i_{H2}$ is corrected by the correction unit 210 to be greater for a higher back pressure of the exhaust gas, acquired by the back pressure acquisition unit 230. As the correction unit 210 corrects the sensor current difference $i_{H2}$ to be greater the higher the back pressure of the exhaust gas, acquired by the back pressure acquisition unit 230, the hydrogen concentration $H_2$ is increased as the back pressure increases. The $H_2$ concentration can be detected with good precision as a result regardless of the state of the exhaust gas.

The specific content of the process being executed in the embodiment will be explained next with reference to FIGS. 2 to 4. FIG. 2 is a flowchart of a routine according to which the gas concentration detection device of the embodiment detects the A/F ratio and $H_2$ concentration in exhaust gas.

In the routine illustrated in FIG. 2 it is determined first whether conditions for executing gas concentration detection are established or not (step 100). Herein, it is determined whether prerequisite conditions for gas concentration detection are established or not, for instance whether the ignition (IG) of the engine is ON, whether the engine is started up, and whether the sensors of the gas concentration detection device 10 are activated. When it is determined that the execution conditions are not established, the process concludes that gas concentration detection cannot be carried out, and the routine ends straightway.

On the other hand, when in step 100 above it is determined the execution conditions for gas concentration detection are established, the process proceeds to the next step, in which there are detected the first sensor current $i_1$ flowing through the sensor cell 9 and the second sensor current $i_2$ flowing through the pump cell 3 (step 102). Next, on the basis of the sensor currents $i_1$ and $i_2$ detected in step 102, a sensor current difference $i_{H2}$ ($=|i_1-i_2|$) is calculated (step 104).

The $H_2$ concentration is acquired next (step 106). FIG. 3 is a map of the relationship between the sensor current difference $i_{H2}$ and $H_2$ concentration. The map of FIG. 3 is stored in the system, specifically the hydrogen concentration detection unit 200. The $H_2$ concentration is detected by the hydrogen concentration detection unit 200 with respect to the sensor current difference $i_{H2}$, in accordance with the above map. The hydrogen concentration detection unit 200 correlates the difference between the first sensor current $i_1$ and the second sensor current $i_2$ (the sensor current difference $i_{H2}=|i_1-i_2|$) to the $H_2$ concentration contained in the map of the relationship between the sensor current difference $I_{H2}$ and $H_2$ concentration.

The A/F ratio is acquired next (step 108). FIG. 4 is a map of the relationship between the sensor current $i_2$ and the A/F ratio. The map of FIG. 4 is stored in the system. The A/F ratio is specified herein with respect to the sensor current $i_2$, in accordance with the above map.

In the embodiment, as explained above, the value of the sensor current $i_2$ in the series of the embodiment is unaffected by the $H_2$ component in the exhaust gas, even when the content of $O_2$ component in the exhaust gas is low. As a result, the $H_2$ concentration can be detected accurately regardless of the A/F ratio of the exhaust gas.

In the system of the embodiment, moreover, the first sensor 1 and the second sensor 2 function also as ordinary A/F ratio sensors. In particular, the output of the second sensor 2 is not affected by the $H_2$ component. Using the sensor current $i_2$ of the second sensor 2 allows detecting an accurate A/F ratio from which the influence of co-existing gases such as $H_2$ is eliminated.

The gas concentration detection device 10 in the embodiment described above, as illustrated in FIG. 1, has a structure in which the first sensor 1 and the second sensor 2 are integrated together with being tandemly-arranged in the up-down direction of the device. The structure of the gas concentration detection device 10, however, is not limited thereto. The gas concentration detection device 10 may have a structure in which the first sensor 1 and the second sensor 2 are disposed close to each other. Specifically, the first sensor 1 and the second sensor 2 may be integrated together with being arranged parallel in the lateral direction of the device, or may not be integrated, but may be simply disposed close to each other.

Figure 5B:
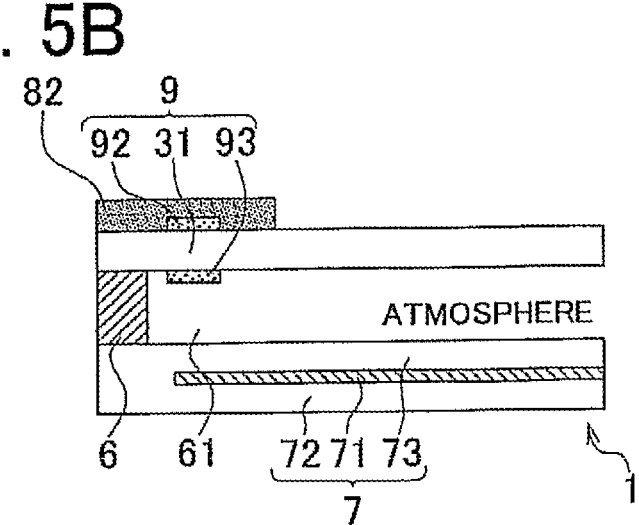
Figure 5C:
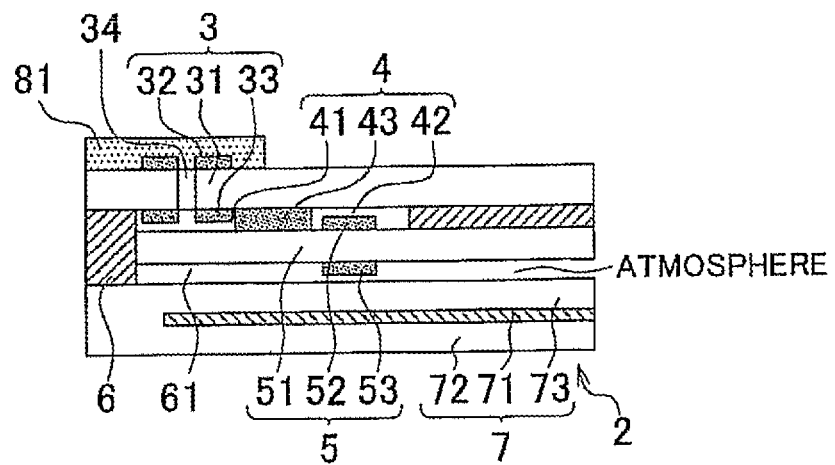

FIGS. 5A to 5C are diagrams illustrating a modification of the structure of the gas concentration detection device 10. FIG. 5A depicts a diagram in which the gas concentration detection device 10 is observed from the stacking direction, FIG. 5B depicts a cross-sectional diagram of FIG. 5A along 5B-5B, and FIG. 5C depicts a cross-sectional diagram of FIG. 5A along 5C-5C. The elements in FIGS. 5A to 5C that are common to those of FIG. 1 are referred to with the same reference numerals, and an explanation thereof is omitted. As illustrated in FIGS. 5A to 5C, the gas concentration detection device 10 has the first sensor 1 and the second sensor 2 integrated side by side. In such a structure, the first sensor 1 and second sensor 2 may be integrated together as is the case in the gas concentration detection device illustrated in FIG. 1.

In the gas concentration detection device 10 of the embodiment, the porosity of diffusion resistance layers 82, 43 is adjusted in such a manner that the gas diffusion influence of the exhaust gas that reaches the surface of the first sensor electrode 92 and the gas diffusion influence of the exhaust gas that reaches the surface of the first sensor electrode 52 are equal, so that the first sensor current $i_1$ and the second sensor current $i_2$ are detected under equal exhaust gas conditions. However, equalization of exhaust gas conditions upon sensor current detection is not limited to the above method. Specifically, the gas concentration detection device 10 may be configured in such a manner that the difference between the gas diffusion influence of the exhaust gas that reaches the sensor electrodes 92, 52 is eliminated by correcting the first sensor current $i_1$, the second sensor current $i_2$, or the sensor current difference $i_{H2}$ between the foregoing.

In the above-described embodiment, the diffusion resistance layer 82 functions as the "resistance layer" of the invention, the first sensor electrode 92 functions as the "electrode" of the invention, the first sensor 1 functions as the "first sensor" of the invention, the inner spaces 41, 42 function as the "gas chamber" of the invention, the sensor cell 5 functions as the "sensor cell" of the invention, and the second sensor 2 functions as the "second sensor" of the invention. The process in step 106 executed by the system functions as the "hydrogen concentration detection unit" of the invention.

In the above-described embodiment, the diffusion resistance layer 43 functions as the "resistance layer" of the invention, the inner space 42 function as the "first gas chamber" of the invention, and the inner space 41 function as the "second gas chamber" of the invention.

What is claimed is:

1. A gas concentration detection device, comprising:
   a first sensor having a resistance layer exposed to a gas to be detected, and an electrode covered by the resistance layer, the first sensor producing an output according to a gas component ratio on a surface of the electrode;
   a second sensor having a pump cell that pumps oxygen into a gas chamber that contains part of the gas to be detected or discharges oxygen out of the gas chamber, and a sensor cell that produces an output according to a gas component ratio in the gas to be detected within the gas chamber, the second sensor producing an output on the basis of a current flowing through the pump cell when the pump cell is operated such that the output of the sensor cell is a predetermined value; and
   a hydrogen concentration detection unit that detects a hydrogen concentration in the gas to be detected on the basis of an output difference between the output of the first sensor and the output of the second sensor.

2. The gas concentration detection device according to claim 1, wherein the hydrogen concentration detection unit includes a correction unit that corrects a relationship between the output difference and the hydrogen concentration on the basis of at least one of temperature and back pressure of the gas to be detected.

3. The gas concentration detection device according to claim 2, wherein the correction unit includes a temperature acquisition unit that acquires a temperature of the gas to be detected, and the correction unit performs a correction such that as the acquired temperature rises, the hydrogen concentration corresponding to the output difference increases.

4. The gas concentration detection device according to claim 2, wherein the correction unit includes a back pressure acquisition unit that acquires a back pressure of the gas to be detected, and the correction unit performs a correction such that as the acquired back pressure increases, the hydrogen concentration corresponding to the output difference increases.

5. The gas concentration detection device according to claim 1, wherein
   the second sensor further includes a diffusion layer that separates the gas chamber into a first gas chamber in which an electrode of the sensor cell is exposed, and a second gas chamber in which an electrode of the pump cell is exposed, and wherein the resistance layer and the diffusion layer have gas diffusion characteristics such that at least one of temperature and back pressure of the gas that reaches the surface of the electrode of the sensor cell is equivalent to the at least one of temperature and back pressure of the gas that reaches the surface of the electrode of the first sensor.

6. The gas concentration detection device according to claim 1, wherein the first sensor and the second sensor are formed integrally with each other.

7. The gas concentration detection device according to claim 1, wherein the hydrogen concentration detection unit detects the hydrogen concentration in the gas to be detected on the basis of a difference between a current flowing through the first sensor and the current flows through the pump cell.

* * * * *